United States Patent [19]

Campbell et al.

[11] 4,379,454
[45] Apr. 12, 1983

[54] DOSAGE FOR COADMINISTERING DRUG AND PERCUTANEOUS ABSORPTION ENHANCER

[75] Inventors: Patricia S. Campbell; Santosh K. Chandrasekaran, both of Palo Alto, Calif.

[73] Assignee: ALZA Corporation, Palo Alto, Calif.

[21] Appl. No.: 235,068

[22] Filed: Feb. 17, 1981

[51] Int. Cl.³ .............................................. A61M 7/00
[52] U.S. Cl. .................................... 604/897; 128/156
[58] Field of Search ................. 128/155–156, 128/260–261, 268; 424/22, 28

[56] References Cited

U.S. PATENT DOCUMENTS

| 3,731,683 | 5/1973 | Zaffaroni | 128/268 |
| 4,060,084 | 11/1977 | Chandrasekaran | 128/260 |
| 4,096,239 | 6/1978 | Katz et al. | 128/260 |
| 4,230,105 | 10/1980 | Harwood | 128/156 |
| 4,286,592 | 9/1981 | Chandrasekaran | 128/156 |
| 4,291,014 | 9/1981 | Keith et al. | 128/268 |

Primary Examiner—C. Fred Rosenbaum
Attorney, Agent, or Firm—Steven F. Stone; Edward L. Mandell; Paul L. Sabatine

[57] ABSTRACT

A dosage form that coadministers a drug and a percutaneous absorption enhancer to a defined area of the skin. The dosage form comprises a body that contains supplies of drug and enhancer and has a basal surface that contacts the area of skin and transmits the drug and enhancer to the area for absorption thereby. The drug is provided to the basal surface at a rate at least as great as the rate at which the skin is able to absorb the drug whereas the enhancer is via a rate controlling means at a substantially constant rate that increases the permeability of the treated area of skin to the drug to a level at which the drug is absorbed at a therapeutically effective rate.

16 Claims, 9 Drawing Figures

DOSAGE FOR COADMINISTERING DRUG AND PERCUTANEOUS ABSORPTION ENHANCER

DESCRIPTION

TECHNICAL FIELD

The invention is a dosage form for administering drugs percutaneously. It is particularly useful for administering estradiol percutaneously.

BACKGROUND ART

The practicality of administering a given drug percutaneously on a continuous basis depends upon the concentration of drug in the blood that is required to provide the desired therapy, how permeable the skin is to the drug, and the amount of skin surface area that is available for administration. The available skin surface area, while theoretically not being limited, is for patient acceptance reasons typically confined to more than about 5 $cm^2$ and less than about 100 $cm^2$. With available area fixed in this range, the matter narrows to whether sufficient drug will pass through that much area to provide the desired therapy. If it will, it is simple to effectively administer the drug percutaneously. If, however, the inherent permeability of the skin to the drug is so high or so low that too much or too little drug will pass through that area of skin, the rate of administration of the drug to the skin must be controlled or the permeability of the skin to the drug must be increased, as the case may be, to make percutaneous administration practical. The present invention involves a situation in which the permeability of the skin to the drug is increased.

There is a great deal of literature concerning compounds that enhance the percutaneous absorption of drugs. Typically a given amount of the enhancer is applied to the skin together with a given amount of the drug in a formulation that has no ability to control the rates at which the enhancer and drug are administered to the skin surface. In such instances more drug and more enchancer are present at the skin surface than the skin can absorb. Thus both drug and enhancer pass through the skin at maximum rates which are likely to be in excess of that needed to provide the desired therapeutic result.

U.S. Pat. No. 4,031,894 suggests pre- or coadministration of percutaneous absorption enhancers in connection with the controlled percutaneous administration of scopolamine. The enhancer is applied to eliminate the stratum corneum as a rate-affecting barrier to scopolamine absorption. To do this the enhancer must elevate the skin permeability to a level at which scopolamine is capable of moving through the skin faster than it is being applied to the skin surface by the system described in the patent. Thus the scopolamine permeates through the skin at the rate at which it is administered to the skin surface. In this type of application the scopolamine administration rate is said to be controlled by the system rather than by the skin. Correlatively, the enhancer administration rate (when coadministered with scopolamine) may be either system-controlled or skin-controlled, but in either case is of such magnitude as to make the scopolamine administration rate system-controlled.

U.S. Pat. No. 3,797,494 describes bandages for administering drugs percutaneously in which the drug may be mixed with a transport agent that enhances the penetration of the skin by the drug. The main components of these bandages are a backing layer, a drug reservoir layer, a microporous membrane layer, and a contact adhesive layer. The patent indicates that the rate of drug administration is controlled by the rate at which drug diffuses from the reservoir through the microporous membrane. These bandages operate, therefore, in the same manner as those described in U.S. Pat. No. 4,031,894. The drug administration rate is controlled by the bandage rather than by the rate at which drug is absorbed by the skin.

U.S. Pat. No. 3,053,255 discloses a multilayer unit for administering drugs percutaneously that is composed of the following layers beginning with the one closest to the skin: a fibrous carrier layer in which the drug is absorbed; an impervious separator layer; a reservoir layer in which a liquid transport agent that is a solvent for the drug is absorbed; and an impervious cover layer. One or more wicks run between the reservoir layer and the carrier layer and serve as a conduit for the flow of transport agent from the former to the latter. In operation the transport agent flows from the reservoir layer to the carrier layer via the wicks. The transport agent dissolves drug absorbed in the carrier layer as it passes therethrough and then, together with dissolved drug, is absorbed by the skin. The cross-sectional area of the wicks "must be such that at least so much of the vehicle can flow therethrough (including the active agent dissolved therein) as will be absorbed by the skin from the active agent carrier." This quote indicates that the amounts of drug and transport agent presented to the skin are equal to or greater than the amounts that the skin can absorb.

DISCLOSURE OF INVENTION

The invention is a unit dosage form and method that coadminister a drug and a percutaneous absorption enhancer to a predetermined area of skin. The drug is administered to the skin at a rate at least as great as the rate at which the skin is capable of absorbing it while the percutaneous absorption enhancer is administered at a substantially constant rate that increases the permeability of the treated area of skin to the drug to a magnitude such that sufficient drug is absorbed to provide a therapeutically effective level of drug in the bloodstream. Accordingly the rate of drug administration is controlled by the rate at which the skin absorbs the drug whereas the rate of percutaneous absorption enhancer administration is controlled by the rate at which the enhancer is released from the dosage form to the skin surface. The rate of drug administration is, therefore, controlled indirectly by the controlled corelease of the enhancer since the latter affects the rate at which the skin will absorb the drug.

More specifically the dosage form comprises a body
(a) having a basal surface
  (i) of area at least about equal to the area of skin to be treated,
  (ii) that is adapted to contact the area of skin over the time period, and
  (iii) via which the drug and enchancer are presented to the area of skin for absorption thereby;
(b) containing a supply of the drug that communicates with the basal surface to provide drug at the basal surface over the time period such that over a substantial portion of the time period the amount of drug provided to the basal surface is in excess of that which the area of skin is able to absorb;

(c) containing a supply of the percutaneous absorption enhancer that communicates with the basal surface so as to provide the enhancer at the basal surface over said time period; and (d) including means for maintaining the rate at which the enhancer is provided at the basal surface substantially constant over a substantial portion of the time period, the rate being
  (i) below the maximum rate the area of skin is able to absorb, and
  (ii) sufficient to increase the permeability of the area of skin to the drug such that the drug is absorbed thereby at a rate that provides a therapeutically effective level of the drug in the bloodstream of the patient.

Correlatively the method comprises
(a) administering the drug to the area continuously over the time period such that over a substantial portion of the time period the amount of drug administered is in excess of that which the area of skin is able to absorb; and (b) simultaneously and continuously coadministering a percutaneous absorption enhancer to the area of skin at a rate that is substantially constant over a substantial portion of the time period, the rate being
  (i) below the maximum rate the area of skin is able to absorb, and
  (ii) sufficient to increase the permeability of the area of skin to the drug such that the drug is absorbed thereby at a rate that provides a therapeutically effective level of the drug in the bloodstream of the patient.

As used herein the term "substantial portion of the time period" means at least about 60% of the time period, preferably at least about 90% of the time period. Correlatively, the term "substantially constant" means a variation of less than about +20%, preferably less than about +10%, over a substantial portion of the time period.

The above described dosage form and method are especially useful for coadministering estradiol and ethanol percutaneously to treat conditions associated with natural estradiol deficiency, such as osteoporosis and headaches, nausea, depression, hot flashes, and other discomforts that often occur during menopause.

BRIEF DESCRIPTION OF THE DRAWINGS

In the drawings, which are not to scale.

MODES FOR CARRYING OUT THE INVENTION

Figure 1:
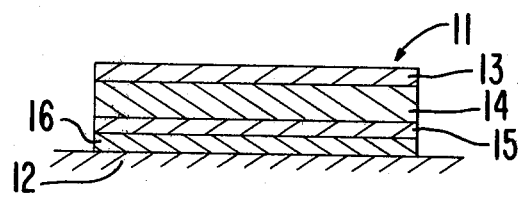
FIG. 1 is an enlarged sectional schematic view of a first embodiment of the invention.

FIG. 1 illustrates a self-adhering skin patch 11 that is designed to be placed on unbroken skin 12. Patch 11 is a laminate that consists of four layers: a top backing layer 13; a drug-enhancer reservoir layer 14, a diffusion membrane layer 15, and a contact adhesive layer 16. Backing layer 13 defines the top of the patch. It is made from a material or combination of materials that is substantially impermeable to the components of reservoir lamina 14. It serves as a protective cover for the patch, keeps the components of reservoir lamina 14 from escaping from the bandage, and fulfills a structural support function. Examples of materials that may be used to make layer 13 are high and low density polyethylene, polypropylene, polyvinylchloride, and polyethylene terephthalate. In embodiments of the invention in which reservoir layer is fluid, the outer edge of the backing layer will overlay the edge of the reservoir layer and be sealed by adhesion or fusion to the diffusion membrane layer. In such structures the reservoir layer is contained wholly between the backing layer and the membrane layer and does not have any exposed surfaces. The backing and diffusion membrane layers will be inherently sealable to each other or will include sealing means, such as an additional layer or adhesive, in such embodiments.

Reservoir layer 14 is immediately below backing 13. It contains supplies of both the percutaneous absorption enhancer and the drug. The amount of drug in the reservoir will depend on the rate at which the drug is absorbed by the skin from the bandage and the intended duration of therapy. Correlatively, the amount of enhancer in the reservoir will depend upon the rate at which the enhancer is administered to the skin from the bandage to achieve the desired degree of drug permeability enhancement over the treatment period. Reservoir layer 14 may include diluents, stabilizers, vehicles, gelling agents, and the like in addition to the drug and enhancer.

In the embodiment of the invention that coadministers estradiol and ethanol the principal components of lamina 14 are estradiol and ethanol. The estradiol is present either wholly in solution or in both dissolved and undissolved particulate form dispersed uniformly through a continuous ethanol phase. The continuous phase contains estradiol over the lifetime of the bandage and the minimum amount of estradiol in layer 14 will depend on its solubility in the continuous phase and the intended lifetime of the bandage. Typically about 0.2 to 12 mg estradiol will be contained in the reservoir layer. Similarly, the minimum amount of ethanol in layer 14 is that which is sufficient to provide a substantially constant flux of about 100 to 800 mcg/cm$^2$/hr, preferably 100 to 400 mcg/cm$^2$/hr, of ethanol to the area of skin being treated over a substantial portion of the intended lifetime of the bandage. The continuous ethanol phase may also contain one or more covehicles, such as water, along with ethanol to alter the solubility of estradiol in the continuous phase. By reducing the solubility of estradiol in the lamina, the quantity of estradiol in the lamina may be reduced significantly. For instance by using water as a covehicle at a 40% by weight level, the quantity of estradiol may be reduced almost two orders of magnitude. Preferably the continuous phase is in the form of a gel that contains 50% to 75% by weight water so that it may be handled easily in manufacturing the bandage. Known gelling agents such as carboxypolymethylene, ethylene maleic anhydride, hydroxyethylcellulose, polyacrylamide, ethylhydroxyethylcellulose, hydroxypropylcellulose, and poly(methylvinylether-maleic anhydride) may be included in the continuous phase to make it gel. The viscosity of these gels are such that the estradiol-ethanol layer should be wholly contained between the backing layer and the diffusion membrane in the manner described above.

Diffusion membrane layer 15, the next layer of the laminate, may be made of a dense or microporous polymer film that has the requisite permeability to the drug and enhancer. It is the member of patch 11 that controls the rate at which the enhancer is administered to the skin. It does not, however, control the rate at which the drug is administered. In other words, it is a principal permeation barrier to the enhancer but not a significant permeation barrier to the drug. The respective fluxes of the drug and enhancer through layer 15 will depend upon the thickness of the layer and its diffusion coefficients relative to the drug and the enhancer. Diffusion coefficients may be determined by standard techniques. Accordingly, films that will permit the required fluxes of drug and enhancer may be selected based on diffusion coefficients and thickness. Preferably the membrane layer 15 is substantially impermeable to other components of the reservoir layer. Examples of the types of polymer films that may be used to make layer 15 are disclosed in U.S. Pat. Nos. 3,797,494 and 4,031,894.

Contact adhesive lamina 16 is directly below diffusion membrane layer 15. It is the means by which bandage 11 is affixed to the area of skin to be treated. Its composition and thickness are such that it does not constitute a significant permeation barrier to the drug and the enhancer. In other words it should be substantially more permeable to the enhancer than layer 15 and at least as permeable to the drug as layer 15. During the time interval between the manufacture and the use of bandage 11, layer 16 may absorb enhancer and drug in amounts that will depend upon the composition and thickness of layer 16 and the length of that time interval. If that interval is quite long, layer 16 will absorb enhancer and drug until it is saturated therewith. The release of such absorbed enhancer from layer 16 once the bandage is applied to the skin may cause the release rate of enhancer from the bandage to exceed the desired steady-state rate for a short period of time. That condition will be transient and will not affect the functionality of the bandage in providing controlled therapy. Contact adhesive compositions that may be used to make layer 16 are disclosed in U.S. Pat. Nos. 3,797,494 and 4,031,894.

Prior to use, bandage 11 also includes a protective undercoating lamina (not shown). Just prior to use, the undercoating lamina is pulled away from lamina 16 and discarded. It is made from materials that are substantially impermeable to the drug, the enhancer, and any other components of layer 16. The same materials that are used to make backing layer 13 may be used to make the undercoating layer, provided they are made strippable such as by siliconizing.

Bandage 11 is applied to a relatively nonhairy area of skin 12 that is substantially free of wrinkles, creases, or folds. Various locations on the torso, such as the flank or shoulder, provide suitable sites for the bandage. As indicated above, once it is placed on the skin the bandage will begin coadministering drug and enhancer to the wearer, with the enhancer being released at a substantially constant rate (following an initial transient surge) and drug being released at the rate at which the enhancer-treated skin is capable of absorbing it. The rate at which the treated skin is capable of absorbing the drug is affected by the enhancer flux through it. Therefore, although drug release is controlled principally by the skin, it is controlled indirectly via the enhancer flux. In the embodiment that coadministers estradiol and ethanol the steady state release rate of ethanol from the bandage is about 100 to 800 mcg/cm$^2$/hr, preferably about 100 to about 400 mcg/cm$^2$/hr. Such rates of ethanol release will permit percutaneous absorption of estradiol at a therapeutically effective rate. In this regard the steady state estradiol concentration in the plasma is incremented by about 15 to 40 pg/ml for every 1 mcg of estradiol administered per hour.

Figure 2:
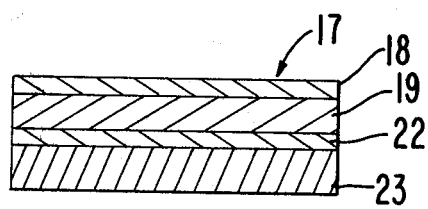
FIG. 2 is an enlarged sectional schematic view of a second embodiment of the invention.

FIG. 2 depicts another embodiment, generally designated 17, of the invention in which the drug and enhancer are stored in separate reservoirs. Embodiment 17 is a laminate composed of four layers: a backing layer 18, a percutaneous enhancer reservoir layer 19, a diffusion membrane layer 22, a drug reservoir-contact adhesive layer 23. Layer 18 is identical in structure and function to layer 13 of embodiment 11. Layer 19 contains the supply of percutaneous absorption enhancer. As in embodiment 11, the amount of enhancer in layer 19 will depend on the rate of enhancer administration required to achieve the desired degree of drug permeability enhancement. It may include diluent, stabilizers, vehicles, gelling agent, and other formulation aids in addition to the enhancer. Layer 22 is the component of bandage 17 that controls the release rate of enhancer to the skin. In this regard it is structurally compositionally, and functionally similar to membrane 15 of embodiment 11. Since the drug does not pass through layer 22, layer 22 need not be permeable to the drug. Indeed it is preferred that it be substantially impermeable to the drug to minimize upward migration of the drug from the drug reservoir layer 23. Layer 23 contains the supply of drug admixed with a contact adhesive composition, with the amount of drug depending on the rate at which the drug is absorbed by the skin and the duration of therapy. The contact adhesive composition may be the same material as is used to make layer 16 of embodiment 11. Alternatively, layer 23 may be separated into a distinct drug reservoir layer composed of the drug supply and a suitable matrix material and a distinct contact adhesive layer underlying the drug reservoir layer.

Embodiments such as bandage 17 in which the drug and enhancer supplies are separate may be advantageous or necessary in instances where formulation or storage of the drug and enhancer in contact with each other is impractical or undesirable or where separation of the drug and enhancer facilitate selection of the diffusion membrane.

Figure 3:
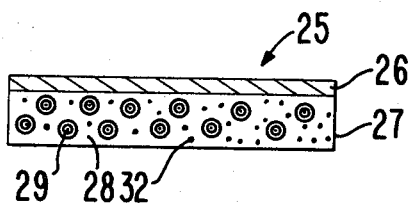
FIG. 3 is an enlarged sectional schematic view of a third embodiment of the invention.

FIG. 3 illustrates another embodiment, generally designated 25, in which the supplies of drug and enhancer are separate. Embodiment 25 is a laminate composed of two layers: a backing layer 26 and a heterogeneous microcapsule-containing basal layer 27. Backing layer 26 is structurally, compositionally, and functionally identical to layer 13 of embodiment 11. Heterogeneous basal layer 27 is composed of a continuous matrix phase 28 in which enhancer-containing microcapsules 29 and drug 32 (represented by stippling in FIG. 3) are dispersed. Continuous matrix phase 28 is a solid, semisolid or gel composition that is permeable to the enhancer and the drug. It preferably adheres to skin. If it does not, an adhesive overlay will have to be used to keep embodiment 25 in contact with the skin. The contact adhesive compositions that are used to make the contact adhesive layers of embodiment 11 and 17 will usually be suitable for use as continuous matrix phase 28. Microcapsules 29 each consist of an inner core of percutaneous absorption enhancer encapsulated by a diffusion membrane. The diffusion membrane functions as diffusion membranes 15 and 22 and may be made of the same materials and be selected based on the same criteria as membranes 15 and 22. Accordingly the diffusion membrane on each microcapsule controls the rate at which the enhancer from all the microcapsule controls the rate at which the enhancer is released therefrom. The combined release of enhancer from all the microcapsules in turn defines the rate of release of enhancer from embodiment 25. As in the case of the other embodiments the amount of enhancer contained in layer 27 in microcapsule form will depend upon the required enhancer release rate and duration of therapy. Microcapsules 29 may be made using conventional microcapsule forming techniques. Drug 32 is present in continuous phase 28 in dissolved or in both dissolved and undissolved forms. The amount of drug present in layer 27 is in excess of that required to provide a continuous source of drug at the skin surface. The particular amount present in a given instance will depend upon the rate at which the drug is absorbed by the skin from layer 27 and the duration of therapy. The thickness and composition of continuous phase 28 should be such that the phase does not constitute a principal permeation barrier to either the enhancer or the drug.

Figure 4:
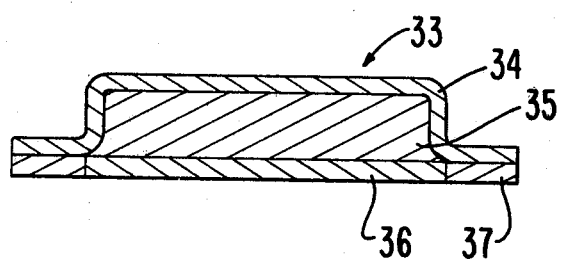
FIG. 4 is an enlarged sectional schematic view of a fourth embodiment of the invention.

FIG. 4 shows another embodiment of the invention, generally designated 33. The components of embodiment 33 are backing layer 34, a reservoir layer 35 that contains supplies of percutaneous absorption enhancer and drug, a diffusion membrane layer 36, and a peripheral ring 37 of contact adhesive. Embodiment 33 is structurally, functionally, and compositionally identical to embodiment 11 except in the following respects. First, the contact adhesive component of embodiment 33 is in the form of a peripheral ring rather than a continuous basal layer. Neither drug nor enhancer passes through ring 37 and it, therefore, need not be permeable to those compositions. Secondly, in embodiment 33 the basal surface from which drug and enhancer is transferred to the skin is defined by diffusion membrane layer 36. Thirdly, the backing layer is not flat but instead forms a pocket or cavity in which the reservoir layer is held. Lastly, the outer edge of the backing layer is sealed to the peripheral ring of contact adhesive.

Figure 5:
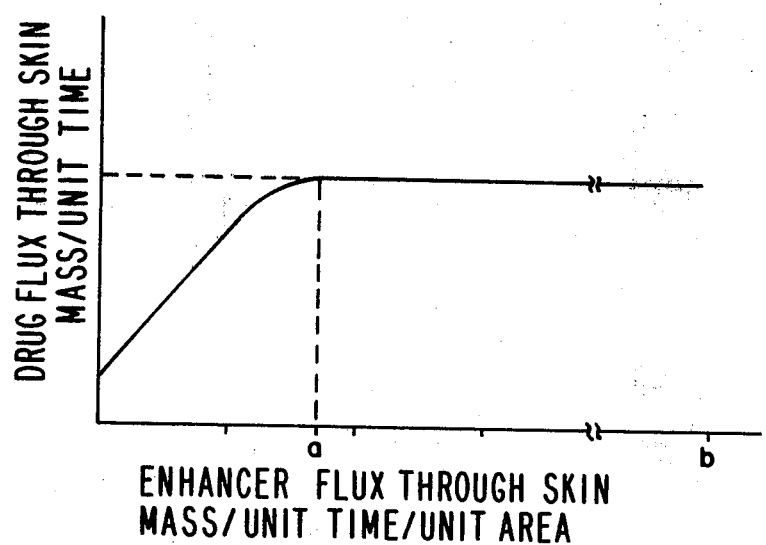
FIG. 5 is a graph illustrating the relationship between the drug flux through skin and the enhancer flux through skin that is typical for many drug-enhancer combinations.

The embodiments of FIGS. 1-4 may be designed to administer drug and enhancer at optimum rates to achieve the desired therapy. In order to determine the optimum rates for a given drug-enhancer combination it is necessary to determine the relationship between the drug flux through the skin and the enhancer flux through the skin. FIG. 5 shows a plot of enhancer flux versus drug flux that is typical for many combinations. Drug flux increases substantially linearly at enhancer fluxes between 0 and "X". At enhancer flux "X" the drug flux levels off at "Y" and is not increased by further increases in the enhancer flux above "X". An optimum design for embodiments involving drug-enhancer combinations having such a relationship will employ an enhancer flux slightly above X. At that enhancer flux, drug flux is at a maximum and is unaffected by minor perturbations in the enhancer flux.

The following examples further illustrate the dosage form of the invention, its manufacture, and its operation. These examples are not intended to limit the invention in any manner. Unless indicated otherwise proportions are by weight.

EXAMPLE 1

Bandages that coadminister ethanol and estradiol were made as follows. A solution of estradiol in 95% ethanol was prepared by mixing 0.0315 part 17-β-estradiol in 1.000 part 95% ethanol. That mixture was gelled by adding 0.0210 part hydroxypropyl-cellulose (mw 1000000, sold under the trademark Klucel) with mixing.

Next, a contact adhesive composition was made by mixing polyisobutene (mw 1200000), polyisobutene (mw 35000), and light mineral oil in a weight ratio of 1:1.25:2. A 50 micron thick layer of that contact adhesive was cast onto a 75 micron thick film of siliconized polyethylene terephthalate. The contact adhesive side of the resulting two-layer subassembly was laminated to a 50 micron-thick film of ethylene-vinyl acetate (EVA) copolymer (9% vinyl acetate). The resulting three-layer subassembly was cut into 15 cm×11 cm pieces. Four 400 mg portions of the gelled estradiol-ethanol mixture were placed equally spaced on the EVA copolymer side of each piece and a 63.5 micron thick backing film for aluminized polyethylene terephthalate with an EVA heat sealable coating was laid over the gels. The backing film was heat sealed to the EVA copolymer layer at the periphery of each piece at 130° C., 27 kg. Finished bandages were punched from laminate with a 4 cm diameter circular punch.

Figure 6:
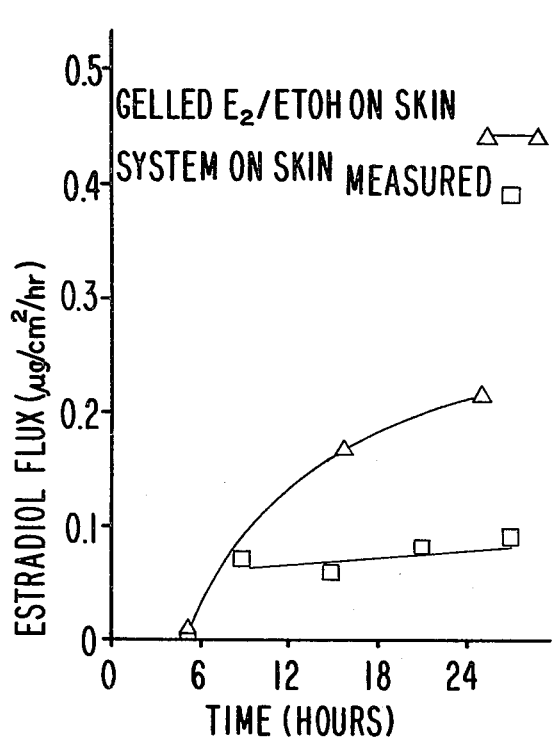
FIG. 6 is a graph of estradiol fluxes versus time for the bandage of Example 1 and for a gelled estradiol-ethanol mixture.
Figure 7:
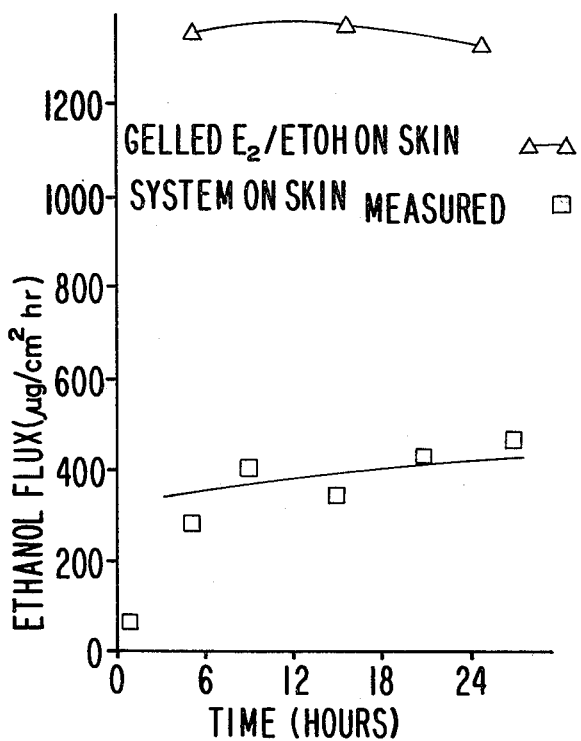
FIG. 7 is a graph of ethanol fluxes versus time for the bandage of Example 1 and for a gelled estradiol-ethanol mixture.

In vitro tests were carried out determine the flux of estradiol and ethanol from the above described bandages using the basic techniques described by Chandrasekaran, et al, Am. Inst. Chem. Eng. J., 22, 828 (1976). Estradiol concentration in the receptor liquid was assayed chromatographically. For comparison the same tests were carried out by applying a 2 ml layer of the above described gelled estradiol-ethanol mixture on the stratum corneum side of the skin mounted in the diffusional cells. FIGS. 6 and 7 are plots of the results of those tests, with FIG. 6 showing the estradiol fluxes and FIG. 7 showing the ethanol fluxes. As shown the estradiol flux from the gelled estradiol-ethanol mixture was nonlinear despite a very high, substantially constant ethanol flux. In contrast both the estradiol and ethanol fluxes were substantially constant from the bandages.

Figure 8:
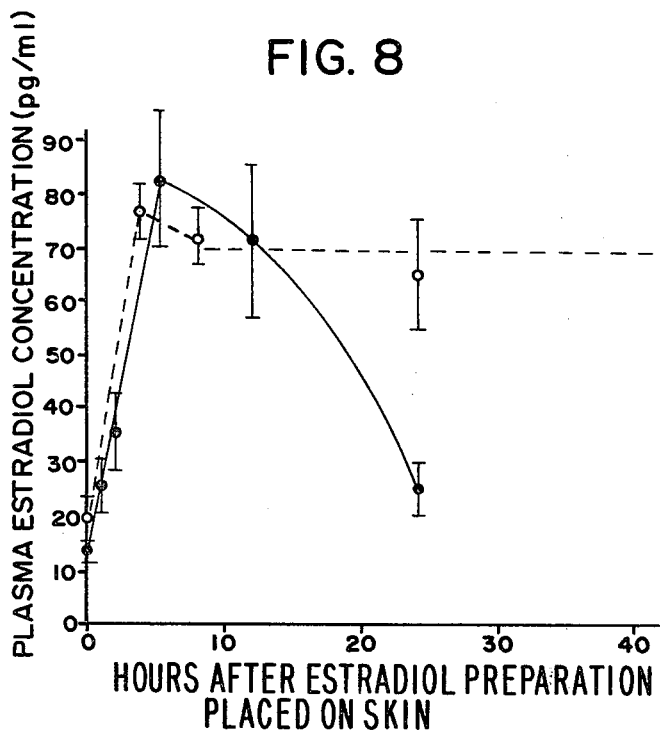
FIG. 8 is a graph showing the plasma estradiol concentration resulting from estradiol administration via the invention and via a commercial ointment.

In vivo tests were carried out by applying two of the above described bandages to the flank skin of 4 postmenopausal subjects. The results were compared with those reported by Strecker, et al., Maturitas, 1:183–190 (1979). These reported tests were carried out by applying Oestrogel ointment as prescribed to the abdominal skin (a portion containing 3000 mcg estradiol was rubbed onto a 400 cm² area of skin). In the tests on the invention bandages plasma samples were taken from the subjects at regular time intervals and analyzed by radioimmunoassay for estradiol content. FIG. 8 is a plot of the results of those analyses together with the reported values for the ointment. As shown, estradiol administration via the bandages caused the concentration of estradiol in the plasma to rise rapidly to about 70 pg/ml and hold at that level. In contrast estradiol administration via the ointment caused the concentration of estradiol in the plasma to rise rapidly to about 80 pg/ml and then continuously drop off over the succeeding 20 hr to about 25 pg/ml.

EXAMPLE 2

The dependence of estradiol flux on ethanol flux in the bandage was illustrated by the following tests.

Figure 9:
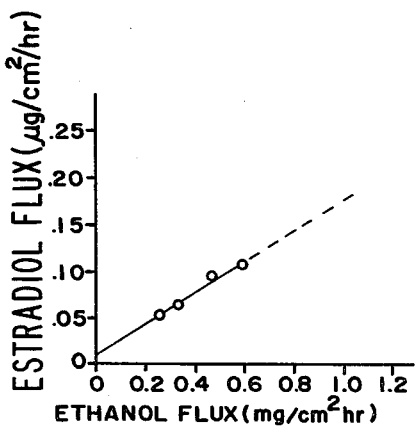
FIG. 9 is a graph of estradiol fluxes versus ethanol fluxes for the bandages of Example 2.

Four bandages were made as in Example 1 except that the ethanol concentration was varied to vary the ethanol flux. In vitro ethanol and estradiol fluxes from these bandages were determined by the procedure of Example 1. These determinations are plotted in FIG. 9. As shown, estradiol flux is directly proportional to ethanol flux over the indicated ethanol flux range.

EXAMPLE 3

This example illustrates the use of water as a covehicle with ethanol in the reservoir. Three sets of bandages were made as in Example 1 except that a 12% rather than a 9% vinyl acetate EVA film was used and 95% ethanol was replaced with ca 75:25, 60:40, and 50:50 w/w ethanol-water mixes. Estradiol content per bandage was 8.5 mg, 3.6 mg, and 1.3 mg, respectively. In vitro tests were carried out as in Example 1 and the ethanol and estradiol fluxes were comparable to those of the bandages of Example 1.

As described and shown above, the embodiments of the invention may be used to conveniently elevate the concentration of estradiol in the plasma to constant levels. In this regard, it is believed that total plasma estradiol levels in the range of about 25 to 60 pg/ml are most advantageous for treating conditions associated with menopause and that levels in the range of about 25 to 40 pg/ml will be most advantageous for treating postmenopausal conditions associated with the natural decrease in estradiol after the ovaries cease functioning. Thus, to treat a given patient one first determines the extent to which the concentration must be elevated to reach the above treatment levels. One then administers a bandage having an effective surface area that will provide the estradiol flux that will achieve the required degree of elevation. Based on the estradiol flux per unit area of skin treated and the elevation of estradiol in the plasma per 1 mcg estradiol administered per hour that are described above, it is apparent that the surface area of skin treated will typically be in the range of 5 to 20 cm².

EXAMPLE 4

Bandages that coadminister ethanol and estradiol were made as follows. A solutin of estradiol in 95% ethanol was prepared by mixing 2 g of estradiol in 100 ml in 95% ethanol. A gelled solution of esthanol was prepared by mixing 215.5 g of 95% ethanol with 353.5 g of water and adding 0.5 g hydroxypropyl-cellulose (mw 1,000,000 sold under the trademark Klucel) while mixing.

Next, a contact adhesive composition was made by mixing polyisobutene (mw 1200000), polyisobutene (mw 35000), and light mineral oil in a weight ratio of 1:1.25:2. A 50 micron thick film of siliconized polyethylene terephthalate. The contact adhesive side of the resulting two-layer subassembly was laminated to a 38 micron-thick film of ethylene-vinyl acetate (EVA) copolymer (12% vinyl acetate). The resulting three-layer subassembly was cut into 8 cm × 5 cm pieces. A 580 mg portion of the gelled ethanol mixture and a 20 mg portion of the estradiol solution in ethanol were placed equally spaced on the EVA copolymer side of each piece and a 45.7 micron thick backing film of polyethylene terephthalate with an EVA heat sealable coating was laid over the gels. The backing film was heat sealed to the EVA copolymer layer at the periphery of each piece at 150° C., 23 kg. Finished bandages were punched from laminate with a 4 cm diameter circular punch.

Modifications of the above described invention that are within the skill of those working in the pharmaceutical, chemical, and/or medical arts are intended to be within the scope of the following claims.

We claim:

1. A unit dosage form for coadministering a drug and a percutaneous absorption enhancer to a predetermined area of unbroken skin of a patient for a predetermined time period, the dosage form comprising a body
   (a) having a basal surface
      (i) of area at least about equal to the area of skin,
      (ii) that is adapted to contact the area of skin over the time period, and
      (iii) via which the drug and enhancer are presented to the area of skin for absorption thereby;
   (b) containing a supply of the drug that communicates with the basal surface to provide drug at the basal surface over the time period such that over a substantial portion of the time period the amount of drug provided is in excess of that which the area of skin is able to absorb;
   (c) containing a supply of the percutaneous absorption enhancer that communicates with the basal surface over said time period; and
   (d) including means for maintaining the rate at which the enhancer is provided at the basal surface substantially constant over a substantial portion of the time period, the rate being
      (i) below the maximum rate the area of skin is able to absorb, and
      (ii) sufficient to increase the permeability of the area of skin to the drug such that the drug is absorbed thereby at a rate that provides a therapeutically effective level of the drug in the bloodstream of the patient.

2. The unit dosage form of claim 1 wherein the basal surface is adhesive to the area of skin.

3. The unit dosage form of claim 1 wherein the supply of drug and the supply of enhancer are admixed and contained in a common reservoir.

4. The unit dosage form of claim 1 wherein the supply of drug and the supply of enhancer are maintained in separate reservoirs.

5. The unit dosage form of claim 1 wherein the means is a diffusion membrane positioned between the supply of enhancer and the basal surface through which the enhancer must permeate to reach the basal surface.

6. The unit dosage form of claim 1 wherein the rate at which the enhancer is provided at the basal surface is above that rate at which the rate of absorption of the drug by the area of skin ceases to increase significantly as the rate at which the enhancer is provided is increased.

7. A unit dosage form for coadministering a drug and a percutaneous absorption enhancer to a predetermined area of unbroken skin of a patient for a predetermined time period comprising a laminate body of:

(a) a backing lamina that is substantially impermeable to drug and enhancer, one face of which defines the uppermost exterior surface of the body;

(b) a reservoir lamina adjacent and below the opposite face that contains a supply of the drug and a supply of the enhancer;

(c) a diffusion membrane lamina adjacent and below the reservoir lamina through which the drug and enhancer permeate; and (d) a contact adhesive lamina adjacent and below the reservoir lamina, one face of which defines a basal surface of the body that contacts and adheres to the area of skin over the time period, and through which the drug and enhancer permeate to the basal surface wherefrom they are absorbed by the area of skin, wherein the compositions and thicknesses of the diffusion membrane lamina and the contact adhesive lamina are such that (i) the drug permeates therethrough over the time period at a rate that provides the drug at the basal surface in excess of that which the area of skin is able to absorb; and (ii) the enhancer permeates therethrough at a substantially constant rate over a substantial portion of the time period, the substantially constant rate being below the maximum rate the area of skin is able to absorb and sufficient to increase the permeability of the area of skin to the drug such that the drug is absorbed by the area of skin at a rate that provides a therapeutically effective level of the drug in the bloodstream of the patient.

8. A dosage form for administering estradiol percutaneously and continuously over a predetermined time period through a predetermined area of unbroken skin of a woman to treat a condition caused by estradiol deficiency comprising a laminate body of:

(a) a backing layer that is substantially impermeable to estradiol and ethanol, one face of which forms the top of the body;

(b) a reservoir layer adjacent the opposite face of the backing layer comprising estradiol dispersed in gelled ethanol;

(c) a diffusion membrane layer adjacent and below the reservoir layer through which estradiol and ethanol are released continuously over said predetermined time period from the reservoir after the body is affixed to the skin, the rate of estradiol release being at least as great as the rate at which said predetermined area of the skin is capable of absorbing estradiol, and the rate of ethanol release being substantially constant and in the range of 100 to 800 mcg/hr/cm$^2$ of said area of skin; and (d) a contact adhesive layer adjacent and below the diffusion membrane layer, one face of which is the basal surface of the body when the body is affixed to the skin, the contact adhesive layer being permeable to estradiol and ethanol.

9. The dosage form of claim 8 wherein the edges of the backing layer and the diffusion membrane layer are sealed together so that the reservoir layer is wholly contained between the backing layer and the diffusion membrane layer.

10. The dosage form of claim 9 wherein the gelled ethanol contains about 5% to about 75% by weight of water.

11. The dosage form of claim 9 or 10 wherein the reservoir layer contains about 0.2 to 12 mg estradiol.

12. The dosage form of claim 9, 10, or 11 wherein the rate of ethanol release is in the range of 100 to 400 mcg/cm$^2$/hr.

13. A method for coadministering a drug and a percutaneous absorption enhancer to a predetermined area of unbroken skin of a patient for a predetermined time period comprising:

(a) administering the drug to the area continuously over the time period such that over a substantial portion of the time period the amount of drug administered is in excess of that which the area of skin is able to absorb; and (b) simultaneously and continuously coadministering a percutaneous absorption enhancer to the area of skin at a rate that is substantially constant over a substantial protion of the time period, the rate being (i) below the maximum rate the area of skin is able to absorb, and (ii) sufficient to increase the permeability of the area of skin to the drug such that the drug is absorbed thereby at a rate that provides a therapeutically effective level of the drug in the bloodstream of the patient.

14. A method for treating a woman for a condition caused by estradiol deficiency comprising:

(a) continuously administering estradiol to a predetermined area of unbroken skin of the said female over a predetermined time period with the rate of administration over a substantial portion of the time period being at least as great as the rate at which said area of skin is capable of absorbing estradiol; and (b) simultaneously and continuously coadministering ethanol to the area of skin at a substantially constant rate in the range of 100 to 800 mcg/hr/cm$^2$ of said area of skin over a substantial portion of the time period.

15. The method of claim 14 wherein the area of skin is about 5 to 20 cm$^2$.

16. The method of claims 14 or 15 wherein said substantially constant rate is in the range of 100 to 400 mcg/cm$^2$/hr.

* * * * *

UNITED STATES PATENT AND TRADEMARK OFFICE
CERTIFICATE OF CORRECTION

PATENT NO. : 4,379,454

DATED : April 12, 1983

INVENTOR(S) : Patricia S. Campbell; Santosh K. Chandrasekaran

It is certified that error appears in the above-identified patent and that said Letters Patent is hereby corrected as shown below:

In the Abstract, line 9, between the words "is" and "via" insert ---transmitted---. In Column 3, line 38, before "20%" change the "+" to---±---, and in Column 3, lines 39 & 40, change the "+" to ---±---. In Column 9, Example 4, line 2, change "solutin" to---solution---. In Column 9, Example 4, line 4, change "esthanol" to---ethanol---.

Signed and Sealed this

Sixteenth Day of April 1985

[SEAL]

Attest:

DONALD J. QUIGG

*Attesting Officer*     *Acting Commissioner of Patents and Trademarks*